(12) United States Patent
Park et al.

(10) Patent No.: US 6,475,773 B2
(45) Date of Patent: Nov. 5, 2002

(54) METHOD FOR PREPARING CHIRAL ESTERS

(75) Inventors: Jai Wook Park; Mahn-Joo Kim; Jeong Hwan Koh, all of Kyongsangbuk-do; Hyun Min Jung, Kongsangbuk-do, all of (KR)

(73) Assignee: Samsung Fine Chemicals Co., Ltd. (KR)

( * ) Notice: Subject to any disclaimer, the term of this patent is extended or adjusted under 35 U.S.C. 154(b) by 0 days.

(21) Appl. No.: 09/726,412

(22) Filed: Dec. 1, 2000

(65) Prior Publication Data

US 2001/0012898 A1 Aug. 9, 2001

(30) Foreign Application Priority Data

Dec. 2, 1999 (KR) ............................................. 99-54472

(51) Int. Cl.⁷ .............................. C12P 41/00; C12P 7/62
(52) U.S. Cl. ....................................... 435/280; 435/135
(58) Field of Search .................................. 435/280, 135

(56) References Cited

PUBLICATIONS

J. American Chem. Soc. 1998, 120, pp 4345–4353 (Mark J. Burk, C.S. Kalberg, and A. Pizzano).
Agnew. Chem. Int. Ed. 1999, 38 No. 4, pp. 516–518 (Q. Jiang, Xiao, Z., Zhang, P. Cao and Xuma Shang).

*Primary Examiner*—Sandra E. Saucier
(74) *Attorney, Agent, or Firm*—Finnegan, Henderson, Farabow, Garrett & Dunner, L.L.P.

(57) ABSTRACT

The present invention relates to a method for preparing a chiral ester and more particularly, the method for preparing an optically pure chiral ester from an alkenyl ester at a high yield by mixing and reacting:

an alkenyl ester; a ruthenium complex to activate reduction reaction of said alkenyl ester and racemization;

a lipase to acylate selectively one of enantiomers of said alkenyl ester; and a reducing agent to supply a hydride to said ruthenium complex. Said optically pure chiral ester of the present invention can be prepared by one-step synthesis from various types of alkenyl esters at a high yield.

7 Claims, No Drawings

METHOD FOR PREPARING CHIRAL ESTERS

BACKGROUND OF THE INVENTION

1. Field of the Invention

The present invention relates to a method for preparing a chiral ester and more particularly, the method for preparing an optically pure chiral ester from an alkenyl ester at a high yield by using an enzyme and a metal catalyst.

It is one of important aims to convert a racemic mixture to an optically pure compound enantioselectively in organic synthesis. Recently, studies for using a metal or an enzyme as a catalyst have been increased in asymmetric syntheses. It has been widely known to use an enzyme as a catalyst for kinetic resolution of a racemic mixture in organic syntheses.

Kinetic resolution is the fact that the two enantiomers react at different rates with a chiral addend. An effective kinetic resolution is the enantioselective conversion from a racemic mixture to an optically pure product (scheme 1), leaving the other enantiomer in the reaction mixture.

Scheme 1

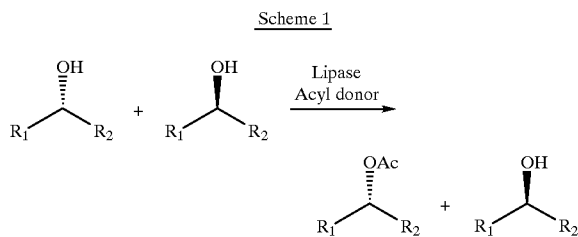

Conventional method for preparing a chiral ester from an alkenyl ester are usually by asymmetric hydrogenation using a catalyst (Mark J. Burk, C. S. Kalberg, and A. Pizzano, *J. Am. Chem. Soc.* 1998, 120, 4345 and Q. Jiang, Xiao, Z. Zhang, P. Cao and Xumu Zhang, *Angew. Chem. Int. Ed. Engl.* 1999, 38, 516). Among these asymmetric hydrogenations, Burk's method introduced that a chiral ester having excellent optical purity was prepared from an alkenyl ester having both a carboxylic acid on α-position of C—C bond and electron deficient C—C bond and Zhang's method introduced that a chiral ester having excellent optical purity was prepared from a cyclic alkenyl ester.

However, when these methods were applied to non-cyclic alkenyl esters, they showed low enantioselectivity.

SUMMARY OF THE INVENTION

Therefore, an object of the present invention is to provide a simple process for preparing optically pure chiral esters from various types of alkenyl esters at a high yield to resolve the above problems.

DETAILED DESCRIPTION OF THE INVENTION

A process for preparing a chiral ester of the present invention is characterized by mixing and reacting: and alkenyl ester;
- a metallic complex, preferably ruthenium complex, more preferably ruthenium complex selected from the group consisting of compounds 1 and 2 expressed in formulas 1 and 2, to achieve reduction reaction of said alkenyl ester and racemization;
- a lipase to acylate selectively one of enantiomers of said alkenyl ester; and
- a reducing agent to supply a hydride to said ruthenium complex.

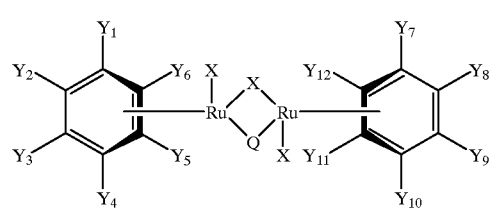

wherein $Y_1$, $Y_2$, $Y_3$, $Y_4$, $Y_5$, $Y_6$, $Y_7$, $Y_8$, $Y_9$, $Y_{10}$, $Y_{11}$, and $Y_{12}$ are a hydrogen atom or a $C_1$–$C_3$ alkyl group; X is Br, Cl or I; and Q is H, Br, Cl, or I.

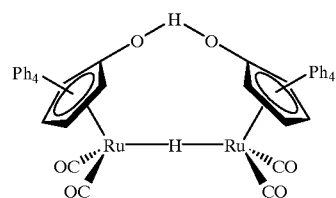

wherein Ph is phenyl.

Said ruthenium complex is selected from the group consisting of the compounds 3 to 5 expressed in the following formulas 3 to 5,

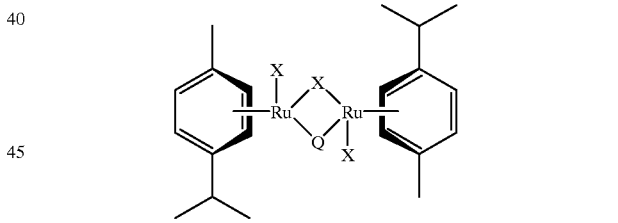

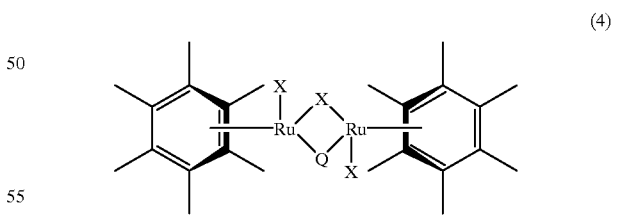

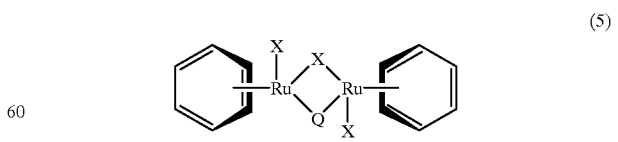

Among the compounds of formulas 3 to 5, a compound of formulas 3a or 3b wherein X is Cl and Q is H or Cl is more preferable,

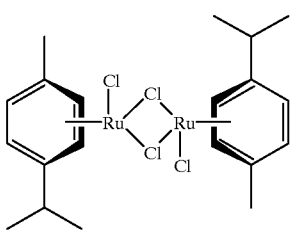

(3a)

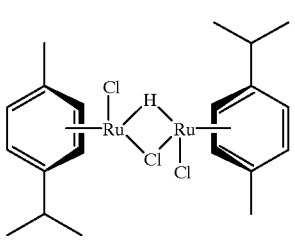

(3b)

A method for preparing a chiral ester from an alkenyl ester is described as follows.

A mixture of a ruthenium complex selected from the group consisting of formulas 1 and 2, a lipase, a reducing agent, and an alkenyl ester is reacted in an appropriate solvent in the presence of a base as shown in Scheme 2. The reaction condition can be varied with a structure of ruthenium complex. For example, when the ruthenium complex of formula 3 where X is Cl and Q is Cl is used, the reaction is performed at a temperature of 40 to 50° C. When the ruthenium complex of formula 3 where X is Cl and Q is H is used, the reaction is performed at a temperature of 40 to 50° C. When the ruthenium complex of formula 2 where X is Cl and Q is Cl is used, the reaction requires 70 to 80° C. of a reaction temperature. The ruthenium complex of formula 3 where X is Cl and Q is Cl is commercially available and is converted to the ruthenium complex of formula 3 where X is Cl and Q is H in alcohol/amine base condition. Therefore, results from the ruthenium complex of formula 5 and the ruthenium complex of formula 8 are almost same. A content of said ruthenium complex is preferred to use 0.1 to 5 mol %, relative to an alkenyl ester. If the content is more than 5 mol %, cost becomes expensive. On the other hand, if it is less than 0.1 mol %, the rate of the reaction becomes too slow.

Scheme 2

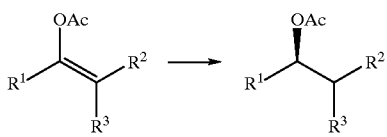

wherein $R^1$, $R^2$ and $R^3$ are, independently, chosen from H, and optionally substituted alkyl, optionally substituted aryl or optionally substituted cycloalkyl group; and $R^1$ and $R^2$, $R^1$ and $R^3$, and $R^2$ and $R^3$ can be cyclized each other, where said substituent of alkyl, aryl and cycloalkyl is a halogen atom or a cyano group.

Said lipase activates deacylation of an alkenyl ester which is a starting material to give the corresponding ketone.

Said ruthenium complex activates reduction reaction of the ketone to the corresponding alcohol by acting as a catalyst to transfer a hydrogen atom and further, activates racemization of the obtained alcohol.

Said lipase, which is an ester hydrolase, acylates one enantiomer from racemic alcohol selectively to a chiral ester. Examples of lipase are *pseudomonas cepacias* lipase and *Candida antarctica* lipase, more preferably, *Candida antarctica* component B lipase supported on acrylic resin (Novozym 435, Novo company) or *Pseudomonas cepacias* lipase supported on ceramic particle (lipase PS-C, Amano company), the most preferably *Candida antarctica* component B lipase supported on acrylic resin for heat resistance, reactivity, optical purity and the like. An amount of said lipase is in the range of 10 to 60 mg, preferably 30 mg, relative to 1 mmol of alkenyl ester in Novozym 435 case, and in the range of 40 to 240 mg, preferably 80 mg, relative to 1 mmol of alkenyl ester in lipase PS-C case.

Said alkenyl ester expressed by the formula 6 is not limited but it is preferred to use the following compounds 6a, 6b, 6c, 6d, 4e, 6f, 6g, or 6h.

(6)

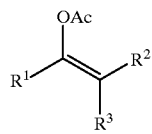

(6a)

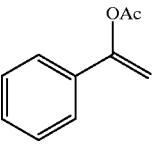

(6b)

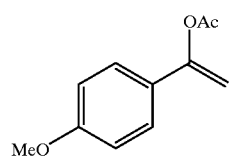

(6c)

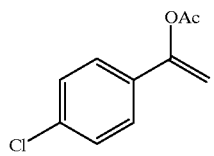

(6d)

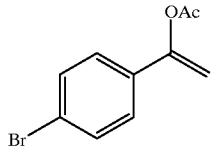

(6e)

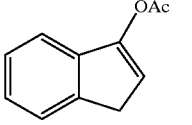

(6f)

-continued (6g)
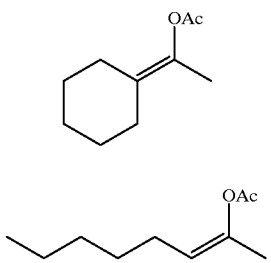

(6h)
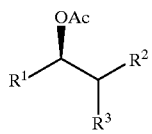

Said reducing agent supplies a hydride to the ruthenium complex. Examples of said reducing agent are 2,6-dimethylheptan-4-ol, hydrogen, and formic acid. Preferred amount of said reducing agent is 1 to 2 equivalents to 1 equivalent to the alkenyl ester. If the content deviates from the range, it inhibits racemization reaction. When said reducing agent is hydrogen gas, it is preferred to be a pressure thereof in the range of 1 to 5 atmosphere. If the pressure is less than 1 atmosphere, the rate of the reduction becomes slow. On the other hand, if it is more than 5 atmospheres, it requires a high-pressure reactor.

A base is also required to remove an acid generated during the reaction. Said base includes triethylamine or diisopropylethyl amine and preferred amount to use is in the range of 1 to 2 equivalents to 1 equivalent to the alkenyl ester.

Reaction solvent is not limited but it is preferred to use methylene chloride, toluene, benzene, or hexane because a solvent commonly affects production yield in an enzyme catalytic reaction. An amount of said solvent is used to be 0.2 to 0.3 M concentration of the alkenyl ester.

A chiral ester expressed in formula 100 is obtained by reacting an alkenyl ester, a ruthenium complex, and a lipase.

(100)
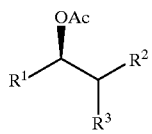

wherein $R^1$, $R^2$ and $R^3$ are, independently, chosen from H, and optionally substituted alkyl, optionally substituted aryl, or optionally substituted cycloalkyl groups; and $R^1$ and $R^2$, $R^1$ and $R^3$, and $R^2$ and $R^3$ can be cyclized with each other, where said substituent of alkyl, aryl and cycloalkyl is a halogen atom or a cyano group.

The chiral ester of formula 100 of the present invention can be used as a synthetic intermediate for preparing various chiral compounds, chiral pharmaceutical drugs or chiral agrochemicals and more particularly, used as an essential intermediate for preparing Aforvastatin expressed in formula 101 which is a useful drug for treatment for hyperlipemia, L-Carnitine expressed in formula 102 which is as an additive used in food and drugs, and Agenerase expressed in formula 103 which is an essential intermediate of AIDS drug.

(101)
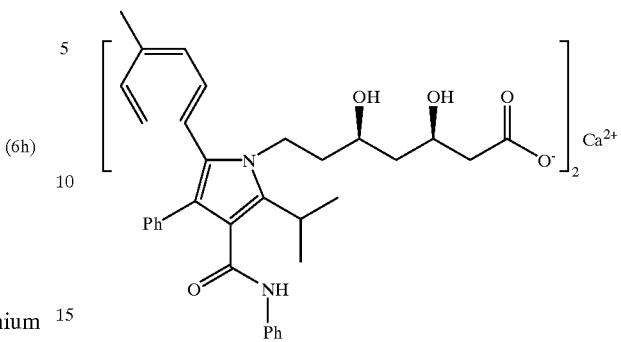

(102)
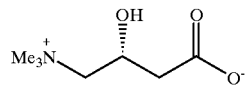

(103)
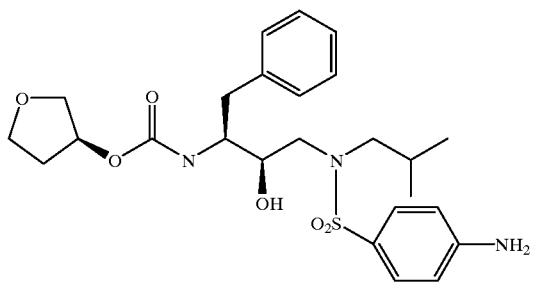

Especially, a chiral compound of formula 100a which is one of the compounds of the present invention is a key intermediate for preparing Aforvastatin of formula 101 disclosed in U.S. Pat. No. 5,908,953, (100a)
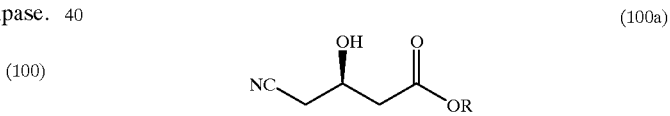

wherein R is a low alkyl group.

The process for preparing a chiral ester of formula 100 of the present invention provides minimum production of by-products such as unreacted alcohol residue up to less than 5% and maximum production of product up to 100% having a high optical purity of 99% or more. Because optical purity is the most important factor in preparing chiral compounds for food and pharmaceutical drugs, the chiral ester of the present invention can be used as a useful starting material in various fields, especially in fine chemical field.

The following examples are intended to be illustrative of the present invention and should not be construed as limiting the scope of this invention defined by the appended claims.

EXAMPLE 1

1-Phenylethenyl acetate of formula 6a (1.00 mmol), ruthenium complex of formula 2 (0.020 mmol), 2,6-dimethylheptan-4-ol (1.50 mmol), and 28 mg of a lipase Nozyme-135 were added to 3.0 ml of toluene. The reaction mixture was stirred to give a yellow suspension.

Argon gas was purged into the reaction suspension, after removing an oxygen under the vacuum condition and then the suspension was heated at 70 C. for 42 hours.

After evaporating a solvent from the reaction mixture, the residue was purified by column chromatography on silica gel to obtain 139 mg of 1-(1-phenylethyl)acetate.

EXAMPLES 2 TO 8

The product, chiral ester, was prepared by the same procedure of Example 1 except to use an alkenyl ester of formulas 6b–6h instead of an alkenyl ester of formula 6a.

EXAMPLE 9

The product, chiral ester, was prepared by the same procedure of Exmample 1 except to use ruthenium complex, where X is Cl and Q is Cl, of formula 3 instead ruthenium complex of formula 2.

EXAMPLES 10 TO 16

The product, chiral ester, was prepared by the same procedure of Example 9 except to use an alkenyl ester of formulas 6b–4h instead of an alkenyl ester of formula 6a.

EXAMPLE 17

1-Phenylethenyl acetate of formula 6a (1.00 mmol), ruthenium complex of formula 2 where (0.020 mmol), and 28 mg of Nozyme 435 were added to 3.0 ml of toluene and stirred to give a yellow suspension.

Oxygen was removed from the reaction suspension under the vacuum condition and further 1 atmosphere of hydrogen gas was injected and then it was heated at 70° C. for 50 hours.

After evaporating a solvent from the reaction mixture, the residue was purified by column chromatography on silica gel to obtain 141 mg of 1-(1-phenylethyl)acetate.

In examples 1 to 8 and example 17 to prepare chiral esters, yield and optical purity of chiral acetates were determined and tabled in Table 1. Said yield of chiral acetate was analyzed by gas chromatography, and said optical purity was determined by high performance liquid chromatography. Said gas chromatography used was Hewlett Packard 5890 Series II and said high performance liquid chromatography was SpectraSystem P2000.

TABLE 1

| Section | Yield (%) | Optical purity (c.c. %) |
| --- | --- | --- |
| Example 1 | 89 | 98 |
| Example 2 | 80 | 98 |
| Example 3 | 91 | 98 |
| Example 4 | 91 | 98 |
| Example 5 | 78 | 98 |
| Example 6 | 92 | 99 |
| Example 7 | 93 | 99 |
| Example 8 | 95 | 91 |
| Example 17 | 86 | 96 |

As shown in Table 1, examples 1 to 8 and example 17 proved that the present invention provides one-step synthesis for preparing an optically pure chiral ester at a high yield from an alkenyl ester by controlling ruthenium complex and lipase. Further, an acyl donor compound is not used in the reaction at all.

What is claimed is:

1. A process for preparing a chiral ester expressed in formula 100 by mixing and reacting:
   an alkenyl ester expressed by formula 6;
   a ruthenium complex selected from the group consisting of compounds 1 and 2 expressed in formulas 1 and 2 to activate reduction reaction of said alkenyl ester and racemization;
   a lipase to acylate selectively one of enantiomers of said alkenyl ester; and
   a reducing agent to supply a hydride to said ruthenium complex,

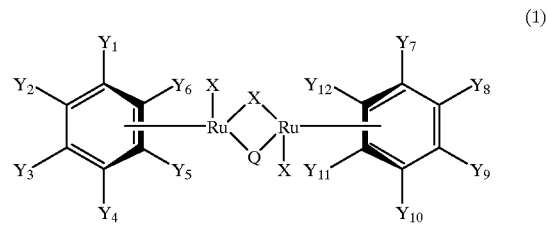

(1)

wherein $Y_1$, $Y_2$, $Y_3$, $Y_4$, $Y_5$, $Y_6$, $Y_7$, $Y_8$, $Y_9$, $Y_{10}$, $Y_{11}$, and $Y_{12}$ are a hydrogen atom or $C_1$–$C_5$ alkyl group; X is Br, Cl or I; and Q is H, Br, Cl, or I;

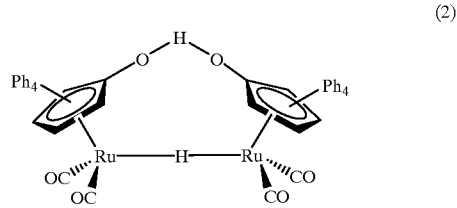

(2)

wherein Ph is phenyl;

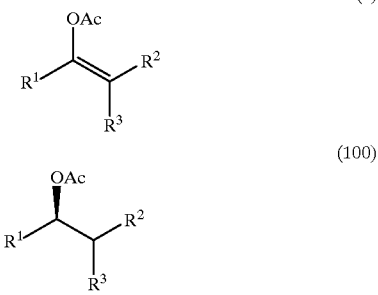

(6)

(100)

wherein $R^1$, $R^2$ and $R^3$ are, independently, chosen from H, and optionally substituted alkyl, optionally substituted aryl, or optionally substituted cycloalkyl groups; and $R^1$ and $R^2$, $R^1$ and $R^3$, and $R^2$ and $R^3$ can be cyclized with each other, where said substituent of alkyl, aryl and cycloalkyl is a halogen atom or a cyano group.

2. The process for preparing a chiral ester according to claim 1, wherein said alkenyl ester is selected from the group consisting of the compounds of formulas 6a to 6h,

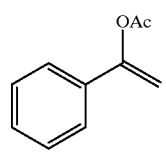

(6a)

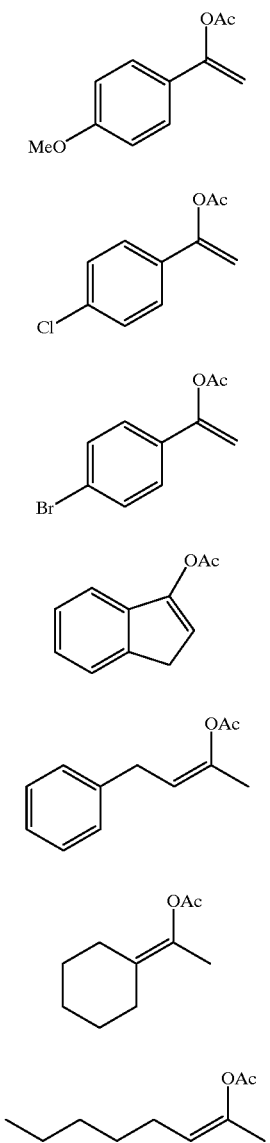

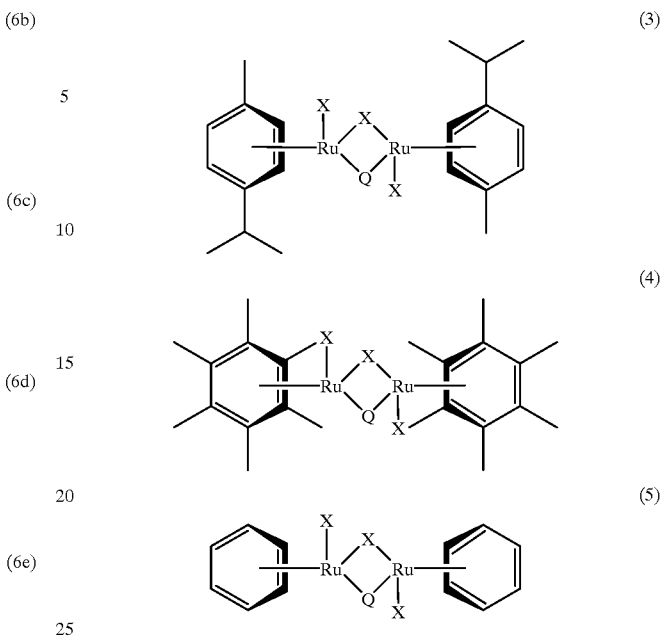

wherein X is Cl, Br or I; and Q is H, Br, Cl or I.

4. The process for preparing a chiral ester according to claim 3, wherein X is Cl and Q is H or Cl for said compound of formulas 3 to 5.

5. The process for preparing a chiral ester according to claim 1, wherein said lipase is selected from the group consisting of *Pseudomonas cepacias* lipase and *Candida antarctica* component B lipase.

6. The process for preparing a chiral ester according to claim 1, wherein said reducing agent is selected from the group consisting of 2,6-dimethylhepthan-4-ol, hydrogen and formic acid.

7. The process for preparing a chiral ester according to claim 1, wherein a content of said ruthenium complex is in the range of 0.1 to 5 mol %, relative to said alkenyl ester.

3. The process for preparing a chiral ester according to claim 1, wherein said ruthenium complex is selected from the group consisting of compounds of formulas 3, 4, and 5,

* * * * *

UNITED STATES PATENT AND TRADEMARK OFFICE
CERTIFICATE OF CORRECTION

PATENT NO.   : 6,475,773 B2
DATED        : November 5, 2002
INVENTOR(S)  : Jai Wook Park et al.

It is certified that error appears in the above-identified patent and that said Letters Patent is hereby corrected as shown below:

<u>Title page,</u>
Item [75], Inventors, "Kongsangbuk-do" should read -- Kyongsangbuk-do --.

<u>Column 8,</u>
Line 51, "or optionally" should read -- and optionally --.

Signed and Sealed this

Thirteenth Day of May, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,475,773 B2
DATED         : November 5, 2002
INVENTOR(S)   : Jai Wook Park et al.

It is certified that error appears in the above-identified patent and that said Letters Patent is hereby corrected as shown below:

<u>Title page,</u>
Item [75], Inventors, "Kongsangbuk-do" should read -- Kyongsangbuk-do --.
Item [73], Assignee, after "(KR)", insert -- Pohang University of Science and Technology (KR) --.

<u>Column 8,</u>
Line 51, "or optionally" should read -- and optionally --.

This certificate supercedes Certificate of Correction issued May 13, 2003.

Signed and Sealed this

Twenty-second Day of July, 2003

JAMES E. ROGAN
*Director of the United States Patent and Trademark Office*